(12) United States Patent
Krishnan et al.

(10) Patent No.: US 9,644,015 B2
(45) Date of Patent: May 9, 2017

(54) CODON OPTIMIZED SEQUENCE FOR AN ANTIVIRAL PROTEIN

(71) Applicant: BioGenomics Limited, Thane West (IN)

(72) Inventors: Archana Rajesh Krishnan, Thane (IN); Sanjay Madhukar Sonar, Thane (IN); Damodar Krishnabahadur Thappa, Thane (IN)

(73) Assignee: BIOGENOMICS LIMITED, Thane West, MH (IN)

( * ) Notice: Subject to any disclaimer, the term of this patent is extended or adjusted under 35 U.S.C. 154(b) by 0 days.

(21) Appl. No.: 14/388,917

(22) PCT Filed: Mar. 28, 2013

(86) PCT No.: PCT/IN2013/000203
§ 371 (c)(1),
(2) Date: Sep. 29, 2014

(87) PCT Pub. No.: WO2013/175487
PCT Pub. Date: Nov. 28, 2013

(65) Prior Publication Data
US 2015/0105537 A1    Apr. 16, 2015

(30) Foreign Application Priority Data

Mar. 30, 2012 (IN) .......................... 1017/MUM/2012

(51) Int. Cl.
*C12N 15/19* (2006.01)
*C12N 15/63* (2006.01)
*C12N 1/21* (2006.01)
*C07K 14/56* (2006.01)

(52) U.S. Cl.
CPC .................................. *C07K 14/56* (2013.01)

(58) Field of Classification Search
None
See application file for complete search history.

(56) References Cited

U.S. PATENT DOCUMENTS 4,921,699 A * 5/1990 DeChiara ............... C12N 15/10
                                                        424/85.7
6,610,830 B1 * 8/2003 Goeddel ................ C12N 15/71
                                                        435/69.51

OTHER PUBLICATIONS

Edge et al. (1983), NAR, vol. 21, No. 18. pp. 6419-6435.*

* cited by examiner

*Primary Examiner* — Christine J Saoud
*Assistant Examiner* — Jegatheesan Seharaseyon
(74) *Attorney, Agent, or Firm* — Merchant & Gould P.C.

(57) ABSTRACT

A codon optimized nucleic acid sequence for Interferon Alpha-2a is provided which can be used for expression of Interferon Alpha-2a in *E. Coli.*

6 Claims, 5 Drawing Sheets

```
atgtgtgatc tgcctcaaac ccacagcctg ggtagcaggc gcaccctgat gctcctggca      60
cagatgagga agatctctct tttctcctgc ctgaaggacc gccatgactt cggattcccc     120
caggaggagt ttggcaacca gttccaaaag gctgaaacca tccccgtcct ccacgagatg     180
atccagcaga tcttcaatct cttcagcaca aaggactcat ctgccgcctg ggatgagacc     240
ctcctagaca agttctacac tgaactctac cagcagctga atgacctgga agcctgcgtg     300
atacaggggg tgggcgtgac cgagacccc cactctctat ctgatgaagg aggactccat tctggctgtg     360
aggaagtact tccaacgcat cactctctat ctgaaagaga agaaatacag cccttgcgcc     420
tgggaggttg tccgcgcaga aatcatgcgc tcttttctc tgtcaaccaa cctgcaagaa     480
agtttacgca gtaaggaatg a                                                501
```

Figure 1

```
optimi    1    ATGTGTGATCTGCCTCAAACCCACAGCCTGGGTAGCAGGCGCACCCTGATGCTCCTGGCA    60
              ||||||||||||||||||||||||||||||||||||||||||||||||||||||||||||
Native    1    ATGTGTGATCTGCCTCAAACCCACAGCCTGGGTAGCAGGCGCACCCTGATGCTCCTGGCA    60 optimi    61   CAGATGAGGAAGATCTCTCTTTTCTCCTGCCTCAGGAGGACCGCCATGACTTCGGATTCCCC   120
              ||||||||||||||| |||||||||| |||||||||||||||||||| ||||||||||||
Native    61   CAGATGAGGAAAATCTCTCTTTTCTCCTGCTTCAGGAGGACCGCCATGACTTTGGATTCCCC   120 optimi    121  CAGGAGGAGTTTGGCAACCAGTTCCAAAAGGCTGAAACCATCCCCGTCCTCCACGAGATG    180
              |||||||||||||||||||||||||||||||||||| |||||||||||||||||||||||
Native    121  CAGGAGGAGTTTGGCAACCAGTTCCAAAAGGCTGAAACCATCCCCGTCCTCCACGAGATG    180 optimi    181  CAGGAGGAGTTTGGCAACCAGTTCCAAAAGGCTGAAACCATCCCCGTCCTCCATGAGATG    240
              ||||||||||||||||||||||||||||||||||||||||||||||||||||||||||||
Native    181  ATCCAGCAGATCTTCAATCTCTACACTGAACTCTTCAGCACACAAAGGACTCATCTGCTC    240 optimi    241  ATCCAGCAGATCTTCAATCTCTACACTGAACTCTTCAGCACACAAAGGACTCATCTGCTC    300
              ||||||||||||||||||||||||||||||||||||||||||||||||||||||||||||
Native    241  CTCCTAGACAAGTTCTACACTGAACTCTACACTGAACTCTACCAGCAGCTGAATGACCTG    300 optimi    301  CTCCTAGACAAATTCTACACTGAACTCTACACTGAACTGAATGACCTGAAGCCTGTGTG    360
              ||||||||||||||||||||||||||||||||||||||||||||||||||||||||||||
Native    301  ATACAGGGGGTGGGGGTGACAGAGACTCCCCCTGATGAAGGAGGAACTCCATTCTGGCTG    360 optimi    361  ATACAGGGGGTGGGGGTGACAGAGACTCCCCCTGATGAAGGAGGAGAAATAACAGCCCTTG    420
              ||||||||||||||||||||||||||||||||||||||||||||||||||||||||||||
Native    361  AGGAAGTACTTCCAACGCCATCACTCTCTATCTGAAAGAGAAGAAATACAGCCCTTGTGCC    420 optimi    421  TGGGAGGTTGTCCGCGCAGAAATCATGCGCTCTCTTTTCTCTGTCAACCTGCAAGAA    480
              ||||||||||||||||||||||||||||||||||||||||||||||||||||||||||||
Native    421  TGGGAGGTTGTCAGAGACAGCAGAAATCATGAGATCTTTTTCTTTGTCAACAAACTTGCAAGAA    480 optimi    481  AGTTTACGCAGTAAGGAATGA    501

Native    481  AGTTTAAGAAGTAAGGAATGA    501

Figure 4
```

CODON OPTIMIZED SEQUENCE FOR AN ANTIVIRAL PROTEIN

CROSS REFERENCE TO RELATED APPLICATION

This application claims priority to the pending PCT application PCT/IN2013/000203, filed on 28 Mar. 2013. The pending PCT application PCT/IN2013/000203 is hereby incorporated by reference in its entireties for all of its teachings.

FIELD OF THE INVENTION

The invention is related to the field of molecular biology and gene engineering more specifically it relates to the cDNA optimized for the efficient and improved expression of Interferon alpha protein in E. coli.

BACKGROUND OF THE INVENTION

Interferons are Glycoprotein messengers produced by the host cells of the body in response to the infections. Interferon secretion induces the protective defense mechanisms of the immune system like activation of Natural killer cells and Macrophages there by starting a screening mechanism to identify the infection or tumor cells by inducing antigen representation to T-Lymphocytes.

Interferon alpha-2a proteins are produced by leukocytes. They mainly up regulate the expression of MHC I proteins and allow increase in presentation of peptides derived from viral antigens. This enhances the activation of CD8+ T cells that are the precursors for cytotoxic T lymphocytes (CTLs) and makes the macrophage a better target for CTL-mediated killing. Interferon alpha also induce the synthesis of several key antiviral mediators, including 2'-5' oligoadenylate synthetase (2'-5' A synthetase) and protein kinase R.

This mechanism of Interferon alpha makes it useful for treatment of various diseases like chronic hepatitis C and hairy cell leukemia, chronic phase Philadelphia chromosome (Ph) positive chronic myelogenous leukemia (CML) patients.

Interferon alpha-2b is indicated for the treatment of chronic hepatitis C in patients 3 years of age and older with compensated liver disease.

Interferon alpha-2a is approved for the treatment of chronic hepatitis C and hairy cell leukemia in patients 18 years of age or older.

Production of Recombinant Interferon alpha is done using E. coli as a host. The cDNA coding for Interferon is cloned into vector and the vector is transformed into E. coli to produce the recombinant protein. The protein produced using the gene is low in quantity because of the codon bias of the E. coli towards the genes of the Human origin. Codon bias is due to the differences in the codon usage in the bacterial genome and the human genome. The codons present rarely in the genome of E. coli are bound to have lesser amount of t-RNA and the scarcity of the t-RNA can cause the premature termination of the m-RNA. This will result in inadequate use of the cellular mechanism for production of the mRNA. Low mRNA yield will affect the protein production. Hence there is need to modify the codons of the gene coding for protein to facilitate proper utilization of available tRNA thereby increasing the production of mRNA coding the protein of interest. Increased amount of mRNA will improve the protein production levels.

The codon optimization is done by substituting the rare codons with abundant codons. But sometimes such substitution may result into production of high GC content regions, complementary regions, or internal ribosome entry sites or poly adenylation sites. This can affect the mRNA formation by causing formation of improper mRNA or causing early termination of mRNA. Thus it is necessary to consider various factors which can affect mRNA stability and cause decrease in the expression levels of the mRNA coding for the protein of interest. As the number of changes in the native cDNA increase the chances of introduction of unfavorable regions may increase. The ideal codon optimization strategy involves identifying the locations where the codons can be substituted to improve the yield of expression. The strategy should be applied carefully to avoid substitution of rare codons at certain location where such substitution can negatively impact the mRNA stability and level of protein expression.

For this reason, there is need to produce the codon optimized cDNA sequences coding for Interferon alpha-2a gene and increasing the expression of the protein.

BRIEF DESCRIPTION OF THE FIGURES

FIG. 1 (Sequence ID no 1) illustrates the codon optimized DNA sequence of the optimized Interferon alpha-2a gene.

FIG. 4 illustrates a comparison of the Native cDNA of Interferon alpha-2a sequence with the codon optimized sequence of Sequence ID no 1.

DETAILED DESCRIPTION

Figure 2:
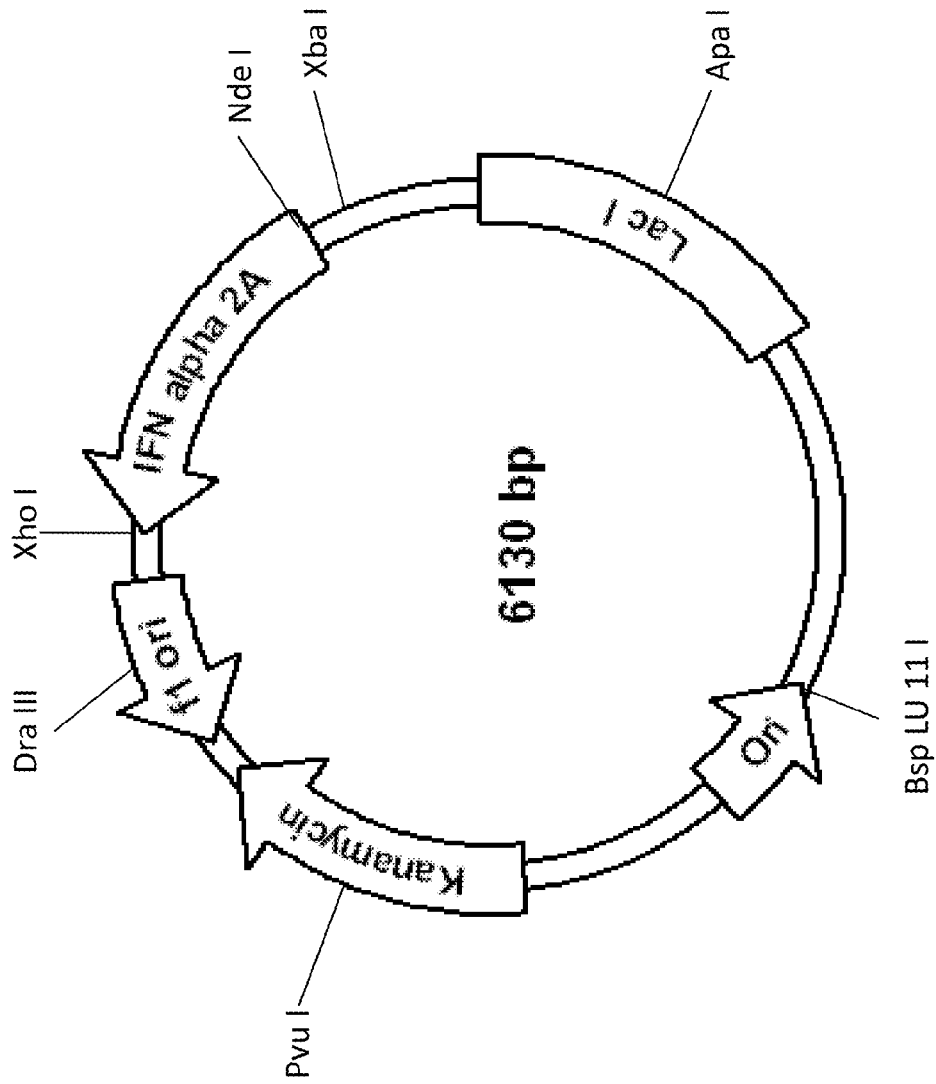
FIG. 2 illustrates the plasmid utilized to express the codon optimized DNA sequence of Interferon alpha-2a in E. coli.

Accordingly the invention provides a polynucleotide of Interferon alpha-2a (Seq ID no 1) (FIG. 1) that provides significantly higher yield of expression of Interferon alpha-2a using E. Coli as host. The yield of Interferon alpha-2a achieved using optimized interferon alpha-2a cDNA is more as compared to the yield achieved using non optimized cDNA of Interferon alpha-2a. Interferon Alpha: The term "interferon-Alpha" or "IFN-Alpha" as used herein refers to Human IFN-Alpha present in the human body and secreted by the leucocytes of the body. The protein is coded by INFA2a gene in humans. Interferon-Alpha can be isolated from natural sources and/or produced by recombinant DNA technology. The said Interferon alpha shall have same sequence homology with, secondary and tertiary structure, bioavailability, potency and the functionality to qualify as a therapeutic biosimilar drug, including bioactivity, of native IFN-Alpha.

Many variants of IFN-Alpha are known in the art. Some mutants are described in details in U.S. patent application Ser. Nos. 11/554,377, 12/542,561, 10/820,467, 10/411,049 incorporated herein by reference herein.

Many methods of cloning and expression of Interferon alpha gene in various hosts like E. coli, Yeast, Animal cells are known in the art. The preferred animal cells are the cell capable of rapidly growth and producing the protein at high expression in continuous cultures, like Chinese hamster ovary cell (CHO).

Expression vectors used for expression of the protein are plasmid, bacterial phage, animal or plant virus, other elements capable of replicating in the host or get integrated in the genome of the host.

Numerous methods are described in the art for expression and purification of Interferon alpha-2a. Some of them are included here by way of reference. U.S. Pat. Nos. 5,196,323, 5,710,027, 7,052,867 Describes method for expression and purification of Interferon alpha-2a in E. coli. U.S. Pat. Nos. 4,680,260, 6,284,520, 7,892,825 describes Process of production of interferon alpha-2a in yeast. U.S. Pat. Nos. 6,159,712, 6,489,144, 4,680,261, 4,966,843 describes method of production of Interferon alpha-2 in mammalian cells.

Codon optimized nucleic acids: Frequency of occurrence of synonymous codons in coding DNA is significantly different in prokaryotic and eukaryotic hosts. This gives rise to significant differences in the composition of their respective genomic tRNA pool in the cytoplasm. When Eukaryotic sequences are cloned into prokaryotic host this factor affects the level of expression of the protein. If the gene insert contains rare codons (codons for which the concentration of the tRNA is less) this can cause a translational pause which can result into detachment of the mRNA from the ribosome. Therefore codon optimization is needed to achieve optimum Expression of the protein in foreign host.

Production of therapeutic proteins using Host Systems like E. coli is carried out to meet the ever increasing demand of therapeutic proteins. Therapeutic proteins produced using such system are costly due to high cost involved in the production of protein. The increase in the level of expression of protein results in production of higher amount of protein per batch thereby reducing the cost of the protein significantly.

EXAMPLE

The following examples are provided to describe the invention and are not intended for reducing the otherwise broad scope of the invention.

Example 1: Codon Optimized cDNA and Vector Containing the Same

Synthetic sequences were synthesized for each individual candidate developed after codon optimization. Such synthetic sequences were cloned into the vector and the said vector was transformed into E. coli (FIG. 2). The expression was analyzed using SDS-PAGE, 2-D gel electrophoresis and other techniques known to the person skilled in the art. The analysis was done for detection of related proteins, no of bands, isoforms of the protein and other properties related to the sequence of the gene. The protein produced was also analyzed as per the test specified in the official monograph of Indian pharmacopeia. Further optimization of the sequence was carried out by identifying the regions on the sequence which are suspected to be contributing for low yield of the protein and substituting the Native codons of the genome with optimized codons. This was done with one amino acid at one time. The expression levels and other properties were analyzed and were compared to the master optimized sequence. If improved expression levels are obtained, then such sequence was used for carrying out further modifications. If further modifications into the sequence results into reduction in the yields of protein or affects other properties of the protein then such modification was avoided. Many such cycles were followed to optimize the sequence.

Figure 3:
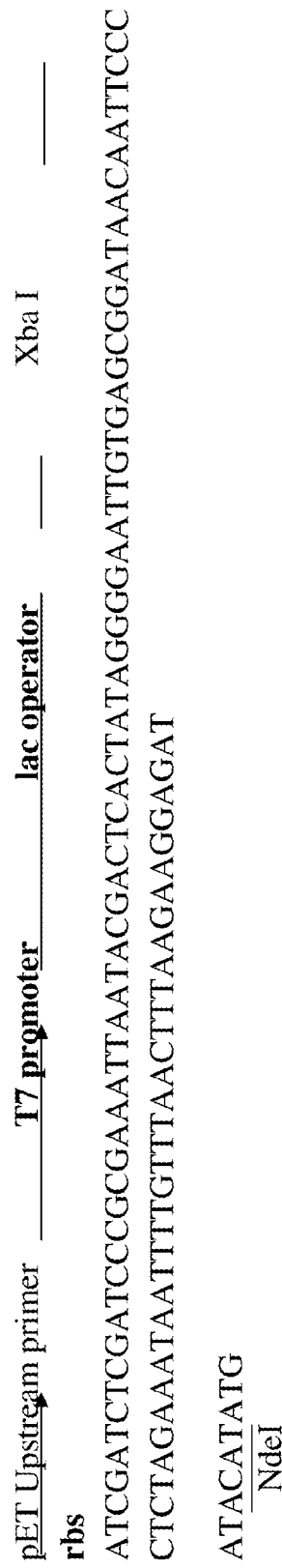
FIG. 3 illustrates the arrangement of the Codon optimized cDNA gene in the plasmid 1. The upstream promoters and other elements of the vector are illustrated.

The flanking restriction sites, NdeI and XhoI were included at the termini of the gene. Following digestion of the synthetic DNA with the restriction enzymes NdeI and XhoI, the 0.503 Kb gene was then ligated via T4 DNA ligase into pBR 322 derived plasmid vector (FIG. 3, FIG. 4), which was also digested with these two enzymes. The recombinant plasmid was then introduced into E. coli strain BL21 (DE3) by transformation (1). The transformation mixture was plated on LB agar plates containing kanamycin (75 micrograms per ml) to allow for selection of colonies containing the pBR 322 derived plasmid/IF-alpha-2a (designated plasmid No. 1). Isolated colonies were further purified by plating and analyzed for IPTG inducible gene expression by standard methods.

Figures 5A, 5B:
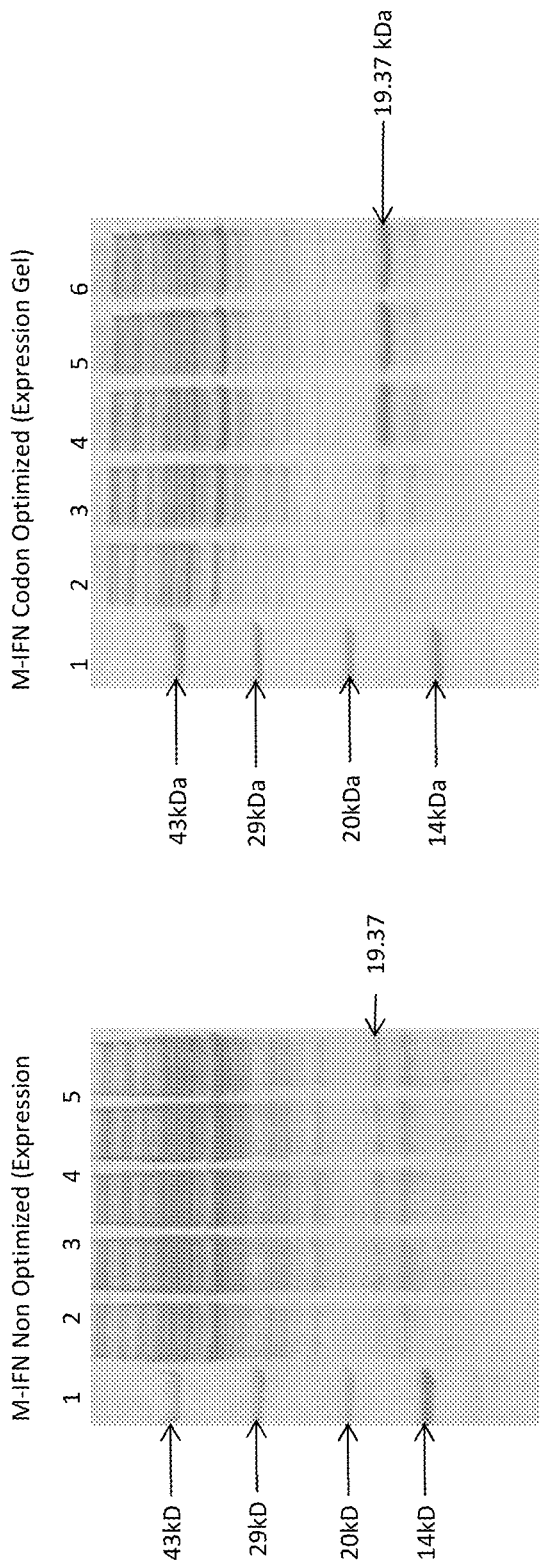
FIGS. 5A and 5B illustrates a comparison of the yields of protein achieved using the codon optimized and Non optimized cDNA sequence.

Example 2: Comparison of Expression Yields Achieved Using Codon Optimized cDNA and Native cDNA The E. coli cells transformed with the vector containing codon optimized cDNA and vector containing native cDNA were grown on the media. The growing cells were subjected to IPTG inducible gene expression and the protein produced was analyzed using SDS PAGE analysis. The yield achieved for expression of the protein using codon optimized cDNA was 10 fold more than the yield achieved using native sequence of IFN alpha-2a as confirmed by SDS PAGE analysis and IMAGE Quant (GE healthcare) (FIGS. 5A and 5B).

What is claimed is:

1. A recombinant nucleic acid molecule comprising the sequence of SEQ ID NO: 1 encoding Human Interferon alpha-2a, or comprising the sequence which is complementary of SEQ ID NO: 1.

2. An expression vector comprising the nucleic acid molecule of claim 1.

3. The expression vector of claim 2 that is a plasmid or a bacterial phage.

4. An *Escherichia coli* host cell comprising the expression vector of claim 2.

5. A method of producing recombinant Human Interferon alpha-2a comprising culturing an *Escherichia coli* host cell comprising an expression vector wherein the expression vector comprises a recombinant nucleic acid molecule with the sequence of SEQ ID NO:1 and isolating Human Interferon alpha-2 produced by the host cell.

6. A recombinant nucleic acid molecule comprising the nucleic acid sequence of SEQ ID NO: 1.

* * * * *

SEQUENCE LISTING

```
<160> NUMBER OF SEQ ID NOS: 2

<210> SEQ ID NO 1
<211> LENGTH: 501
<212> TYPE: DNA
<213> ORGANISM: Artificial Sequence
<220> FEATURE:
<223> OTHER INFORMATION: Codon optimized sequence encoding human
      interferon alpha-2

<400> SEQUENCE: 1
atgtgtgatc tgcctcaaac ccacagcctg ggtagcaggc gcaccctgat gctcctggca      60
cagatgagga agatctctct tttctcctgc ctgaaggacc gccatgactt cggattcccc     120
```

```
caggaggagt ttggcaacca gttccaaaag gctgaaacca tccccgtcct ccacgagatg      180
atccagcaga tcttcaatct cttcagcaca aaggactcat ctgccgcctg ggatgagacc      240
ctcctagaca agttctacac tgaactctac cagcagctga atgacctgga agcctgcgtg      300
atacaggggg tgggcgtgac cgagaccccc ctgatgaagg aggactccat tctggctgtg      360
aggaagtact tccaacgcat cactctctat ctgaaagaga agaaatacag cccttgcgcc      420
tgggaggttg tccgcgcaga aatcatgcgc tcttttttctc tgtcaaccaa cctgcaagaa     480
agtttacgca gtaaggaatg a                                               501

<210> SEQ ID NO 2
<211> LENGTH: 501
<212> TYPE: DNA
<213> ORGANISM: Artificial Sequence
<220> FEATURE:
<223> OTHER INFORMATION: cDNA (native codons) encoding human interferon
      alpha-2a

<400> SEQUENCE: 2
atgtgtgatc tgcctcaaac ccacagcctg ggtagcagga ggaccttgat gctcctggca       60
cagatgagga aaatctctct tttctcctgc ttgaaggaca gacatgactt tggatttccc      120
caggaggagt ttggcaacca gttccaaaag gctgaaacca tccctgtcct ccatgagatg      180
atccagcaga tcttcaatct cttcagcaca aaggactcat ctgctgcttg ggatgagacc      240
ctcctagaca aattctacac tgaactctac cagcagctga atgacctgga agcctgtgtg      300
atacaggggg tgggggtgac agagactccc ctgatgaagg aggactccat tctggctgtg      360
aggaaatact tccaaagaat cactctctat ctgaaagaga agaaatacag cccttgtgcc      420
tgggaggttg tcagagcaga aatcatgaga tcttttttctt tgtcaacaaa cttgcaagaa     480
agtttaagaa gtaaggaatg a                                                501
```